United States Patent [19]

Burkhart et al.

[11] Patent Number: 5,445,724
[45] Date of Patent: Aug. 29, 1995

[54] PHOSPHONIUM SALTS AND USE THEREOF AS BRIGHTENERS FOR AQUEOUS ACIDIC ELECTRONICKELIZATION BATHS

[75] Inventors: Bernd Burkhart, Mutterstadt; Alfred Oftring, Bad Durkheim; Volker Schwendemann, Neustadt; Klaus Glaser, Mannheim, all of Germany

[73] Assignee: BASF Aktiengesellschaft, Ludwigshafen, Germany

[21] Appl. No.: 307,788
[22] PCT Filed: Mar. 23, 1993
[86] PCT No.: PCT/EP93/00695
  § 371 Date: Sep. 30, 1994
  § 102(e) Date: Sep. 30, 1994
[87] PCT Pub. No.: WO93/20087
  PCT Pub. Date: Oct. 14, 1993

[30] Foreign Application Priority Data
  Apr. 3, 1992 [DE] Germany .................. 42 11 140.4

[51] Int. Cl.$^6$ ................... C25D 3/12; C25D 3/16
[52] U.S. Cl. ....................... 205/259; 205/260; 205/274; 205/275; 205/280
[58] Field of Search ............. 205/259, 260, 274, 275, 205/280

[56] References Cited

U.S. PATENT DOCUMENTS 4,076,600 2/1973 Huebner ................. 204/55 R

FOREIGN PATENT DOCUMENTS 1191652 5/1963 Germany .

OTHER PUBLICATIONS

"Praktishce Galvanotechnik", Eugen G. Lenze Verlag, Saulgan, 4th Ed. (1984), pp. 268–271 (no month).

*Primary Examiner*—John Niebling
*Assistant Examiner*—Edna Wong
*Attorney, Agent, or Firm*—Oblon, Spivak, McClelland, Maier, & Neustadt

[57] ABSTRACT

Nickelized shaped articles are produced by electrodeposition of nickel from aqueous acidic baths containing as essential constituents one or more nickel salts, one or more inorganic acids and one or more brighteners by a procedure in which the brighteners used are phosphonium salts I

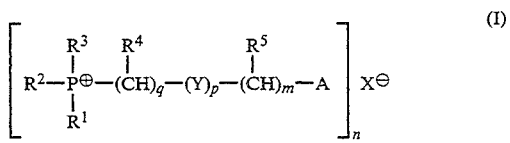

where
 $R^1$ to $R^3$ are each $C_1$–$C_{18}$-alkyl, which may be carboxyl-, $C_1$–$C_4$-alkoxycarbonyl- or cyano-substituted, $C_2$–$C_{12}$-alkenyl, $C_2$–$C_{12}$-alkynyl, $C_5$–$C_8$-cycloalkyl, $C_7$–$C_{12}$-phenylalkyl, phenyl, which may be substituted by one or two substituents selected from the group consisting of $C_1$–$C_4$-alkyl, $C_1$–$C_4$-alkoxy, halogen, hydroxyl, phenyl and $C_1$–$C_4$-alkoxycarbonyl, or mono- or di($C_1$–$C_4$-alkyl)amino,
 $R^4$ and $R^5$ are each hydrogen or $C_1$–$C_4$-alkyl,
 A is hydrogen or a group of the formula —CO—H, —CO—$R^6$, —CO—OH, —CO—O$R^6$, —CO—CH$_2$—CO—O$R^6$, —O—CO—H, —O—CO—$R^6$, —O$R^6$, —SO$_2$—$R^6$, —SO$_2$—OH, —SO$_2$—O$R^6$, —PO(OH)$_2$, —PO(OH)(O$R^6$), —PO(O$R^6$)$_2$, —OPO(OH)$_2$, —OPO(OH)(O$R^6$) or —OPO(O$R^6$)$_2$, where
 $R^6$ is $C_1$–$C_{12}$-alkyl, $C_2$–$C_{12}$-alkenyl, $C_2$–$C_{12}$-alkynyl, $C_5$–$C_8$-cycloalkyl, $C_7$–$C_{12}$-phenylalkyl or phenyl, which may be substituted by one or two substituents selected from the group consisting of $C_1$–$C_4$-alkyl, $C_1$–$C_4$-alkoxy, halogen, hydroxyl, phenyl and $C_1$–$C_4$-alkoxycarbonyl,
 Y is —CH=CH— or —C≡C—,
 m is from 0 to 10,
 n is from 1 to 4,
 p is 0 or 1,
 q is from 0 to 10, and
 $X^\ominus$ is an n-valent inorganic or organic anion that promotes solubility in water.

11 Claims, No Drawings

PHOSPHONIUM SALTS AND USE THEREOF AS BRIGHTENERS FOR AQUEOUS ACIDIC ELECTRONICKELIZATION BATHS

The present invention relates to the use of novel phosphonium salts as brighteners for aqueous acidic electronickelization baths.

It is known that acidic nickel electrolytes must contain small amounts of organic substances if the electronickelization is to produce a bright, ductile and surface-planar deposition of the metal. Such brighteners, which in general are divided into primary and secondary brighteners, are customarily used in the form of combinations comprising a plurality of these agents in order to enhance the effect.

Praktische Galvanotechnik, Eugen G. Lenze Verlag, Saulgau, 4th edition 1984, pages 268 to 271 (1) describes customary brighteners for nickel electrolytes. Although the compounds are classified as primary or secondary brighteners or planarizers, it is admitted at the same time that clear-cut classification is not always possible. The brightening compounds mentioned are:

- sulfonimides, e.g. benzoic sulfimide
- sulfonamides
- benzenesulfonic acids, e.g. mono-, di- and tribenzenesulfonic acid
- naphthalenesulfonic acids, e.g. mono-, di- and trinaphthalenesulfonic acid
- alkylsulfonic acids
- sulfinic acid
- arylsulfone sulfonates
- aliphatic compounds with ethylene and/or acetylene bonds, e.g. butynediol
- single- and multiring nitrogen-containing heterocycles with or without further hetero atoms such as sulfur or selenium
- coumarin
- amines and quaternary ammonium compounds as planarizing agents
- saccharin.

DE-B-1 191 652 (2) describes single- or multiring heterocyclic nitrogen bases of the aromatic type in quaternized form such as pyridinium salts, e.g. 2-pyridinium-1-sulfatoethane, as planarizers, i.e. brighteners, for acidic nickel-plating baths. These agents are used together with customary basic brighteners such as benzene-m-disulfonic acid, diaryldisulfimides or sulfonamides.

U.S. Pat. No. 4,076,600 (3) discloses aqueous acidic zinc electrolyte baths containing phosphonium cations of the formula $R_4P^{\oplus}$ where R is hydroxyalkyl.

In commercial practice, it is customary to combine alkenylsulfonic acids such as sodium vinylsulfonate or sodium allylsulfonate with other brighteners such as propargyl alcohol, 2-butine-1,4-diol, propinesulfonic acid or 3-pyridiniumpropyl sulfonate.

However, the prior art agents generally need to be used in relatively high concentrations in the nickel electrolyte baths used.

It is an object of the present invention to provide an improved process for producing nickelized shaped articles using brighteners that are superior or at least equal in brightening to, for example, 2-pyridinium-1-sulfatoethane or 3-pyridiniumpropyl sulfonate, but can be used in a lower concentration.

We have found that this object is achieved by a process for producing nickelized shaped articles by electrodeposition of nickel from aqueous acidic baths containing as essential constituents one or more nickel salts, one or more inorganic acids and one or more brighteners, which comprises using as brighteners phosphonium salts of the general formula I

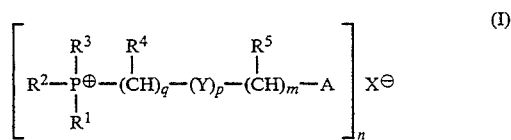

where
$R^1$ to $R^3$ are each $C_1$–$C_{18}$-alkyl, which may be carboxyl-, $C_1$–$C_4$-alkoxycarbonyl- or cyano-substituted, $C_2$–$C_{12}$-alkenyl, $C_2$–$C_{12}$-alkynyl, $C_5$–$C_8$-cycloalkyl, $C_7$–$C_{12}$-phenylalkyl, phenyl, which may be substituted by one or two substituents selected from the group consisting of $C_1$–$C_4$-alkyl, $C_1$–$C_4$-alkoxy, halogen, hydroxyl, phenyl and $C_1$–$C_4$-alkoxycarbonyl, or mono- or di($C_1$–$C_4$-alkyl)amino,
$R^4$ and $R^5$ are each hydrogen or $C_1$–$C_4$-alkyl,
A is hydrogen or a group of the formula —CO—H, —CO—$R^6$, —CO—OH, —CO—O$R^6$, —CO—CH$_2$—CO—O$R^6$, —O—CO—H, —O—CO—$R^6$, —O$R^6$, —SO$_2$—$R^6$, —SO$_2$—OH, —SO$_2$—O$R^6$, —PO(OH)$_2$, —PO(OH)(O$R^6$), —PO(O$R^6$)$_2$, —OPO(OH)$_2$, —OPO(OH)(O$R^6$) or —OPO(O$R^6$)$_2$, where
$R^6$ is $C_1$–$C_{12}$-alkyl, $C_2$–$C_{12}$-alkenyl, $C_2$–$C_{12}$-alkynyl, $C_5$–$C_8$-cycloalkyl, $C_7$–$C_{12}$-phenylalkyl or phenyl, which may be substituted by one or two substituents selected from the group consisting of $C_1$–$C_4$-alkyl, $C_1$–$C_4$-alkoxy, halogen, hydroxyl, phenyl and $C_1$–$C_4$-alkoxycarbonyl,
Y is —CH=CH— or —C≡C—,
m is from 0 to 10,
n is from 1 to 4,
p is 0 or 1,
q is from 0 to 10, and
$X^{\ominus}$ is an n-valent inorganic or organic anion that promotes solubility in water.

Suitable $C_1$–$C_4$-alkyl for $R^4$ and $R^5$ and for substituents on phenyl are n-propyl, isopropyl, n-butyl, isobutyl, sec-butyl, tert-butyl and in particular methyl and ethyl.

Examples of straight-chain or branched $C_1$–$C_{18}$- or $C_1$–$C_{12}$-alkyl for $R^1$ to $R^3$ and $R^6$ to $R^8$ in addition to the abovementioned $C_1$–$C_4$-alkyl radicals are n-amyl, isoamyl, sec-amyl, tert-amyl, neopentyl, n-hexyl, n-heptyl, n-octyl, 2-ethylhexyl, n-nonyl, isononyl, n-decyl, n-undecyl, n-dodecyl, n-tetradecyl, n-hexadecyl and n-octadecyl. Of these, $C_1$–$C_4$-alkyl is preferred.

Examples of suitable carboxyl-, $C_1$–$C_4$-alkoxycarbonyl- or cyano-substituted $C_1$–$C_{18}$-alkyl for $R^1$ to $R^3$ are 2-carboxyethyl, 2-(methoxycarbonyl)ethyl, 2-(ethoxycarbonyl)ethyl and 2-cyanoethyl.

Suitable $C_5$–$C_8$-cycloalkyl for $R^1$ to $R^3$ and $R^6$ to $R^8$ is in particular cyclopentyl, cyclohexyl, cycloheptyl, cyclooctyl, methylcyclopentyl, dimethylcyclopentyl, methylcyclohexyl, dimethylcyclohexyl or ethylcyclohexyl. Of these, preference is given to cyclopentyl and cyclohexyl.

Examples of suitable $C_7$–$C_{12}$-phenylalkyl for $R^1$ to $R^3$ and $R^6$ to $R^8$ are 1-phenylethyl, 2-phenylethyl, 1-phenylpropyl, 2-phenylpropyl, 3-phenylpropyl, 2- phenylprop-2-yl, 4-phenylbutyl, 2,2-dimethyl-2-phenylethyl, 5-phenylamyl, 6-phenylhexyl and in particular benzyl.

In monosubstituted phenyl for $R^1$ to $R^3$ and $R^6$ to $R^8$ the substitution pattern is preferably para and in disubstituted phenyl the substituents are preferably in the 2,4-position, for example as in 2,4-xylyl. If substituents are present, the degree of substitution is preferably 1. But particular preference is given to unsubstituted phenyl.

Suitable $C_1$–$C_4$-alkoxy radicals are in particular methoxy and ethoxy but also n-propoxy, isopropoxy, n-butoxy, isobutoxy, sec-butoxy and tert-butoxy.

Examples of $C_1$–$C_4$-alkoxycarbonyl are n-propoxycarbonyl, isopropoxycarbonyl, n-butoxycarbonyl, isobutoxycarbonyl, sec-butoxycarbonyl, tert-butoxycarbonyl but in particular ethoxycarbonyl and methoxycarbonyl.

The term halogen atom herein encompasses fluorine, iodine and in particular bromine and especially chlorine.

Examples of straight-chain or branched $C_2$–$C_{12}$-alkenyl for $R^1$ to $R^3$ and $R^6$ to $R^8$ are vinyl, allyl, methallyl, 3-butenyl, 4-pentenyl, 5-hexenyl, 7-octenyl, 9-decenyl, 11-dodecenyl, citronellolyl, geraniolyl and linaloolyl.

Examples of suitable straight-chain or branched $C_2$–$C_{12}$-alkynyl for $R^1$ to $R^3$ and $R^6$ to $R^8$ are ethynyl and 2-propynyl.

Examples of suitable mono- or di($C_1$–$C_4$-alkyl)amino for $R^1$ to $R^3$ are methylamino, dimethylamino, ethylamino, diethylamino, n-butylamino and di-n-butylamino.

$R^4$ and $R^5$ are each preferably hydrogen, methyl or ethyl, in particular hydrogen.

m is preferably from 0 to 8, in particular from 0 to 5, especially from 0 to 3.

q is preferably from 0 to 5, in particular 1.

Suitable n-valent anions X are the customary, normally water-solubilizing inorganic or organic anions, in particular chloride, bromide, fluoride, sulfate, hydrogensulfate, methanesulfonate, trifluoromethanesulfonate, 2-hydroxyethanesulfonate, p-toluenesulfonate, nitrate, tetrafluoroborate, perchlorate, 1-hydroxyethane-1,1-diphosphonate, dihydrogenphosphate, hydrogen phosphate, phosphate, formate, acetate, oxalate and tartrate.

Of these, anions with one or two charges (n=1 or 2) are preferred, in particular fluoride, sulfate, methanesulfonate, nitrate and tetrafluoroborate but especially chloride and bromide.

If A is a carboxylic acid, sulfonic acid, phosphonic acid or phosphoric acid function, the phosphonium salts I can also be present as betaines which can be formed by elimination of HX from the phosphonium salts.

A preferred embodiment comprises using phosphonium salts I wherein $R^1$ to $R^3$ are each $C_1$–$C_4$-alkyl or unsubstituted or $C_1$–$C_4$-alkyl-monosubstituted or -disubstituted phenyl. In particular, $R^1$ to $R^3$ are each unsubstituted phenyl.

Another preferred embodiment comprises using phosphonium salts of the general formula I$a$

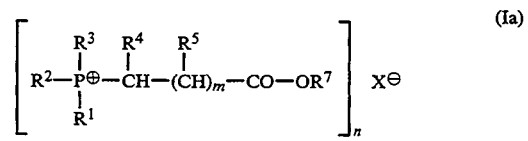

wherein $R^1$ to $R^5$, m, n and $X^\ominus$ are each as defined above and $R^7$ is hydrogen, $C_1$–$C_{12}$-alkyl, $C_2$–$C_{12}$-alkenyl, $C_2$–$C_{12}$-alkynyl, $C_5$–$C_8$-cycloalkyl, $C_7$–$C_{12}$-phenylalkyl or unsubstituted, $C_1$–$C_4$-alkyl-monosubstituted or -disubstituted phenyl.

A further preferred embodiment comprises using phosphonium salts of the general formula I$b$

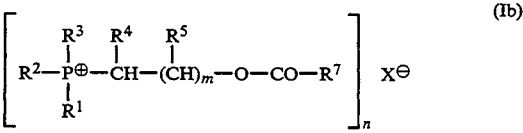

wherein $R^1$ to $R^5$, $R^7$, m, n and $X^\ominus$ are each as defined above.

A further preferred embodiment comprises using phosphonium salts of the general formula I$c$

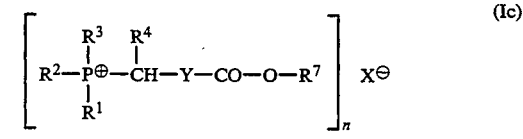

wherein $R^1$ to $R^4$, $R^7$, Y, n and $X^\ominus$ are each as defined above.

A further preferred embodiment comprises using phosphonium salts of the general formula I$d$

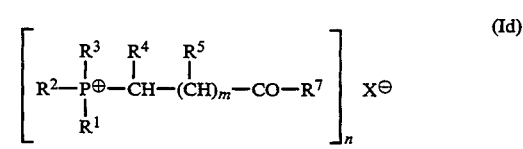

wherein $R^1$ to $R^5$, $R^7$, m, n and $X^\ominus$ are each as defined above.

A further preferred embodiment comprises using phosphonium salts of the general formula I$e$

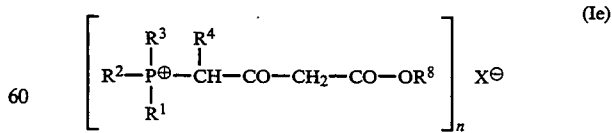

wherein $R^1$ to $R^4$, n and $X^\ominus$ are each as defined above and $R^8$ has the same meanings as $R^7$ with the exception of hydrogen.

A further preferred embodiment comprises using phosphonium salts of the general formula I$f$

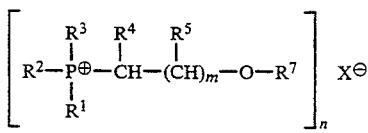

wherein $R^1$ to $R^5$, $R^7$, m, n and $X^\ominus$ are each as defined above.

A further preferred embodiment comprises using phosphonium salts of the general formula I*g*

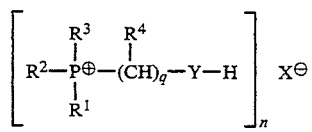

wherein $R^1$ to $R^4$, Y, n, q and $X^\ominus$ are each as defined above.

A further preferred embodiment comprises using phosphonium salts of general formula I*h*

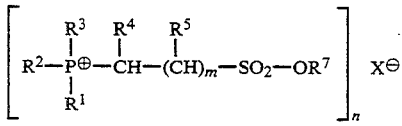

wherein $R^1$ to $R^5$, $R^7$, m, n and $X^\ominus$ are each as defined above.

The phosphonium salts I according to the invention are preparable in an advantageous manner by reacting the corresponding precursor of the general formula II

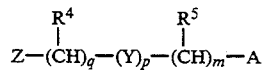

where Z is a nucleofugic leaving group, preferably chlorine or bromine, with a phosphine of the general formula III

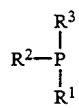

and if desired subsequently exchanging the anion $Z^\ominus$ for $X^\ominus$.

Examples of suitable phosphines III are trimethylphosphine, triethylphosphine, tri-n-butylphosphine, tri-n-octylphosphine, tris(2-ethylhexyl)phosphine, triphenylphosphine, tris(dimethylamino)phosphine, tricyclohexylphosphine, dimethylethylphosphine, diethylmethylphosphine, tris(2-cyanoethyl)phosphine, triisobutylphosphine, tri-n-octadecylphosphine, tris(2-carboxyethyl)phosphine, dibenzylmethylphosphine, diethyl-n-octadecylphosphine, triallylphosphine, tri-n-decylphosphine and tri-n-hexylphosphine.

The reaction of components II and III is advantageously carried out in an inert organic solvent such as toluene, xylene, petroleum ether, naphtha, cyclohexane, acetone, tetrahydrofuran, dioxane, methanol, ethanol, isopropanol, ethyl acetate or methyl benzoate or in a mixture thereof. However, the reaction can also be carried out in water or in a single-phase or two-phase mixture of water and one or more organic solvents, preferably polar organic solvents. In the case of two-phase mixtures it is possible to use a customary phase transfer catalyst. The reaction is in general carried out at from 40° to 130° C. in particular at from 60° to 110° C., under atmospheric pressure.

Since the phosphonium salts I act in a way that is typical of secondary brighteners, they are preferably used combined with further, normally primary, brighteners or else, as the case may be, with one or more further secondary brighteners. Examples of suitable primary brighteners are sodium vinylsulfonate, sodium allylsulfonate, and examples of suitable secondary brighteners are 2-butyne-1,4-diol and propargyl alcohol.

The aqueous acidic nickel electrolyte baths used contain one or usually more than one nickel salt, for example nickel sulfate and nickel chloride, one or more inorganic acids, preferably boric acid and sulfuric acid, as brighteners the compounds I alone or combined with further, customary brighteners and optionally further customary auxiliaries and additives in the concentrations customary therefor, for example wetting agents and pore inhibitors. Customary aqueous acidic nickel electrolytes ("Watts electrolytes") have the following basic composition:

200–350 g/l of $NiSO_4.7\ H_2O$
30–150 g/l of $NiCl_2.6\ H_2O$
30–50 g/l of $H_3BO_3$.

The electrolyte bath pH is customarily within the range from 3 to 6, preferably within the range from 4 to 5. This pH is conveniently set with a strong mineral acid, preferably sulfuric acid.

The compounds I are present in the electrolyte baths in low concentrations, in general within the range from 0.01 to 0.5 g/l, preferably within the range from 0.025 to 0.3 g/l. The concentrations of further, customary brighteners are in each case normally within the range from 0.1 to 10 g/l, in particular from 0.1 to 2.0 g/l.

The nickel electrolyte baths described above can be used to electroplate in particular nickel coatings onto shaped articles made of steel, but also onto shaped articles made of other materials, for example brass, which have been pretreated as usual. The electroplating is in general carried out at from 30° to 80° C., preferably at from 40° to 60° C.

The compounds I of the invention are notable for extremely powerful brightening. In general they produce better brightness than the customary brighteners and, what is more, at a distinctly lower concentration in the nickel electrolyte baths.

PREPARATION EXAMPLES

EXAMPLE 1

Preparation of Benzyl Triphenylphosphonioacetate Chloride 23.6 g (0.1 mol) of triphenylphosphine were suspended in 70 ml of toluene. 18.5 g (0.1 mol) of benzyl chloroacetate were added dropwise and the mixture was heated at the boil for two hours. After cooling down to room temperature, the precipitated product was filtered off and washed with diethyl ether. Drying left 40.8 g (corresponding to a yield of 90%) of the title compound in the form of colorless crystals. The product was more than 99% pure.

EXAMPLE 2

Preparation of 3-(triphenylphosphonio)propyl Methyl Ketone Chloride

The title compound was prepared from triphenylphosphine and 3-chloropropyl methyl ketone as described in Example 1 in a yield of 82%.

EXAMPLE 3

Preparation of 4-(triphenylphosphonio)butyric Acid Chloride

The title compound was prepared from triphenylphosphine and 4-chlorobutyric acid as described in Example 1 in a yield of 78%.

EXAMPLE 4

Preparation of Methyl 4-(triphenylphosphonio)acetoacetate Chloride

The title compound was prepared from triphenylphosphine and methyl 4-chloroacetate as described in Example 1 in a yield of 84%.

EXAMPLE 5

Preparation of Ethyl 5-(triphenylphosphonio)valerate Bromide

The title compound was prepared from triphenylphosphine and ethyl 5-bromovalerate as described in Example 1 in a yield of 74%.

EXAMPLE 6

Preparation of 5-(triphenylphosphonio)valeric Acid Bromide

The title compound was prepared from triphenylphosphine and 5-bromovaleric acid as described in Example 1 in a yield of 79%.

EXAMPLE 7

Preparation of Triphenylphosphoniumallyl Chloride

The title compound was prepared from triphenylphosphine and allyl chloride as described in Example 1 in a yield of 89%.

USE EXAMPLES

The products prepared in Examples 1 to 7 were used as brighteners in weakly acidic electroplating baths for the deposition of nickel.

The aqueous nickel electrolyte used had the following composition:
- 300 g/l of $NiSO_4.7\ H_2O$
- 60 g/l of $NiCl_2.6\ H_2O$
- 45 g/l of $H_3BO_3$
- 2 g/l of saccharin
- 0.8 g/l of vinylsulfonic acid, sodium salt
- x g/l of brightener as per table
- 0.5 g/l of a fatty alcohol derivative of the formula $C_{12}H_{25}/C_{14}H_{29}$—O—$(CH_2CH_2O)_2$—$SO_3Na$ as wetting agent.

The pH of the electrolyte was set to 4.2 with sulfuric acid.

Brass panels were used. Prior to being coated with nickel they had been cathodically degreased in a conventional manner in an alkaline electrolyte. They were nickelized in a 250 ml Hull cell at 55° C. with a current strength of 2A over a period of 10 minutes. The panels were then rinsed with water and dried with compressed air.

The Table below shows the results of these experiments. It can be seen that the brighteners of the invention produced better brightness than the prior art brighteners, in some instances at a distinctly lower concentration in the nickel electrolyte bath.

TABLE

Test results of electronickelization

| Example No. | Brightener | Concentration x [g/l] | Brighteners [rating] |
|---|---|---|---|
| 8 | of Example No. 1 | 0.1 | 5 |
| 9 | of Example No. 2 | 0.05 | 5 |
| 10 | of Example No. 3 | 0.2 | 5 |
| 11 | of Example No. 4 | 0.05 | 5 |
| 12 | of Example No. 5 | 0.05 | 5 |
| 13 | of Example No. 6 | 0.3 | 5 |
| 14 | of Example No. 7 | 0.025 | 5 |
| for comparison | | | |
| A | 2-pyridinium-1-sulfatoethane | 0.3 | 4–5 |
| B | 3-pyridinium-propylsulfonate | 0.3 | 4–5 |

Rating scheme for brightness:
5 = excellent (perfect specular gloss)
4 = good (virtually specular gloss)
3 = moderate
2 = poor
1 = no brightness
Comparative compound A is known from (2).

We claim:

1. A process for producing nickelized shaped articles by electrodeposition of nickel from aqueous acidic baths containing as essential constituents one or more nickel salts, one or more inorganic acids and one or more brighteners, which comprises using as brighteners phosphonium salts of the general formula I

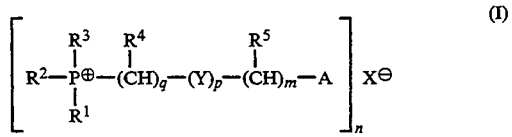

where
$R^1$ to $R^3$ are each $C_1$–$C_{18}$-alkyl, which may be carboxyl-, $C_1$–$C_4$-alkoxycarbonyl- or cyano-substituted, $C_2$–$C_{12}$-alkenyl, $C_2$–$C_{12}$-alkynyl, $C_5$–$C_8$-cycloalkyl, $C_7$–$C_{12}$-phenylalkyl, phenyl, which may be substituted by one or two substituents selected from the group consisting of $C_1$–$C_4$-alkyl, $C_1$–$C_4$-alkoxy, halogen, hydroxyl, phenyl and $C_1$–$C_4$-alkoxycarbonyl, or mono- or di($C_1$–$C_4$-alkyl)amino, $R^4$ and $R^5$ are each hydrogen or $C_1$–$C_4$-alkyl, A is hydrogen or a group of the formula —CO—H, —CO—$R^6$, —CO—OH, —CO—$OR^6$, —CO—$CH_2$—CO—$OR^6$, —O—CO—H, —O—CO—$R^6$, —$OR^6$, —$SO_2$—$R^6$, —$SO_2$—OH, —$SO_2$—$OR^6$, —PO(OH)$_2$, —PO(OH)($OR^6$), —PO($OR^6$)$_2$, —OPO(OH)$_2$, —OPO(OH)($OR^6$) or —OPO($OR^6$)$_2$, where $R^6$ is $C_1$–$C_{12}$-alkyl, $C_2$–$C_{12}$-alkenyl, $C_2$–$C_{12}$-alkynyl, $C_5$–$C_8$-cycloalkyl, $C_7$–$C_{12}$-phenylalkyl or phenyl, which may be substituted by one or two substituents selected from the group consisting of $C_1$–$C_4$-alkyl, $C_1$–$C_4$-alkoxy, halogen, hydroxyl, phenyl and $C_1$–$C_4$-alkoxycarbonyl, Y is —CH=CH— or —C≡C—,
m is from 0 to 10,
n is from 1 to 4,
p is 0 or 1,
q is from 0 to 10, and
X⊖ is an n-valent inorganic or organic anion that promotes solubility in water.

2. A process as claimed in claim 1 wherein $R^1$ to $R^3$ are each $C_1$-$C_4$-alkyl or unsubstituted or $C_1$-$C_4$-alkyl-monosubstituted or -disubstituted phenyl.

3. A process as claimed in claim 1, wherein the phosphonium salts used have the general formula I$a$

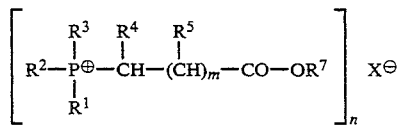
(Ia)

wherein $R^1$ to $R^5$, m, n and X⊖ are each as defined above and $R^7$ is hydrogen, $C_1$-$C_{12}$-alkyl, $C_2$-$C_{12}$-alkenyl, $C_2$-$C_{12}$-alkynyl, $C_5$-$C_8$-cycloalkyl, $C_7$-$C_{12}$-phenylalkyl or unsubstituted, $C_1$-$C_4$-alkyl-monosubstituted or -disubstituted phenyl.

4. A process as claimed in claim 1, wherein the phosphonium salts used have the general formula I$b$

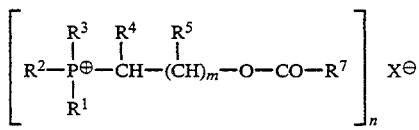
(Ib)

wherein $R^1$ to $R^5$, m, n and X⊖ are each as defined above, and $R^7$ is hydrogen, $C_1$-$C_{12}$-alkyl, $C_2$-$C_{12}$-alkenyl, $C_2$-$C_{12}$-alkynyl, $C_5$-$C_8$-cycloalkyl, $C_7$-$C_{12}$-phenylalkyl or unsubstituted, $C_1$-$C_4$-alkyl-monosubstituted or -disubstituted phenyl.

5. A process as claimed in claim 1, wherein the phosphonium salts used have the general formula I$c$

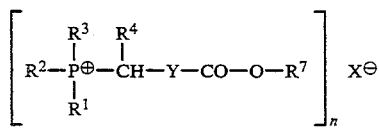
(Ic)

wherein $R^1$ to $R^4$, Y, n and X⊖ are each as defined above, and $R^7$ is hydrogen, $C_1$-$C_{12}$-alkyl, $C_2$-$C_{12}$-alkenyl, $C_2$-$C_{12}$-alkynyl, $C_5$-$C_8$-cycloalkyl, $C_7$-$C_{12}$-phenylalkyl or unsubstituted, $C_1$-$C_4$-alkyl-monosubstituted or -disubstituted phenyl.

6. A process as claimed in claim 1, wherein phosphonium salts used have the general formula I$d$

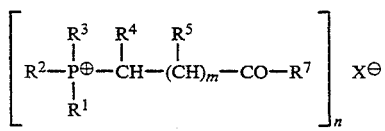
(Id)

wherein $R^1$ to $R^5$, m, n and X⊖ are each as defined above, and $R^7$ is hydrogen, $C_1$-$C_{12}$-alkyl, $C_2$-$C_{12}$-alkenyl, $C_2$-$C_{12}$-alkynyl, $C_5$-$C_8$-cycloalkyl, $C_7$-$C_{12}$-phenylalkyl or unsubstituted, $C_1$-$C_4$-alkyl-monosubstituted or -disubstituted phenyl.

7. A process as claimed in claim 1, wherein the phosphonium salts used have the general formula I$e$

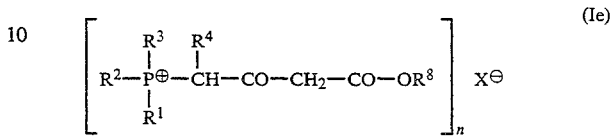
(Ie)

wherein $R^1$ to $R^4$, n and X⊖ are each as defined above and $R^8$ is $C_1$-$C_{12}$-alkyl, $C_2$-$C_{12}$-alkenyl, $C_2$-$C_{12}$-alkynyl, $C_5$-$C_8$-cycloalkyl, $C_7$-$C_{12}$-phenylalkyl or unsubstituted, $C_1$-$C_4$-alkyl-monosubstituted or -disubstituted phenyl.

8. A process as claimed in claim 1, wherein the phosphonium salts used have the general formula I$f$

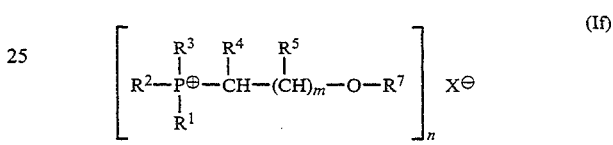
(If)

wherein $R^1$ to $R^5$, m, n and X⊖ are each as defined above, and $R^7$ is hydrogen, $C_1$-$C_{12}$-alkyl, $C_2$-$C_{12}$-alkenyl, $C_2$-$C_{12}$-alkynyl, $C_5$-$C_8$-cycloalkyl, $C_7$-$C_{12}$-phenylalkyl or unsubstituted, $C_1$-$C_4$-alkyl-monosubstituted or -disubstituted phenyl.

9. A process as claimed in claim 1, wherein the phosphonium salts used have the general formula I$g$

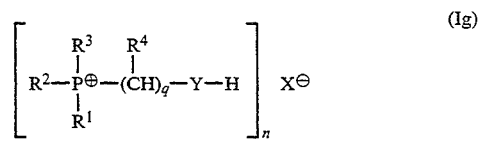
(Ig)

wherein $R^1$ to $R^4$, Y, n, q and X⊖ are each as defined above.

10. A process as claimed in claim 1, wherein the phosphonium salts used have the general formula I$h$

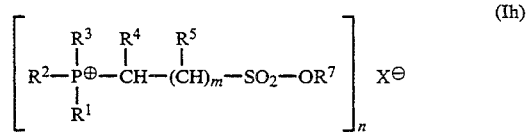
(Ih)

wherein $R^1$ to $R^5$, m, n and X⊖ are each as defined above, and $R^7$ is hydrogen, $C_1$-$C_{12}$-alkyl, $C_2$-$C_{12}$-alkenyl, $C_2$-$C_{12}$-alkynyl, $C_5$-$C_8$-cycloalkyl, $C_7$-$C_{12}$-phenylalkyl or unsubstituted, $C_1$-$C_4$-alkyl-monosubstituted or -disubstituted phenyl.

11. A process as claimed in claim 1, wherein as well as the phosphonium salts I at least one further brightener is used.

* * * * *